April 20, 1954 H. C. SWIM Plant Pat. 1,268
PEACH TREE
Filed Jan. 26, 1953
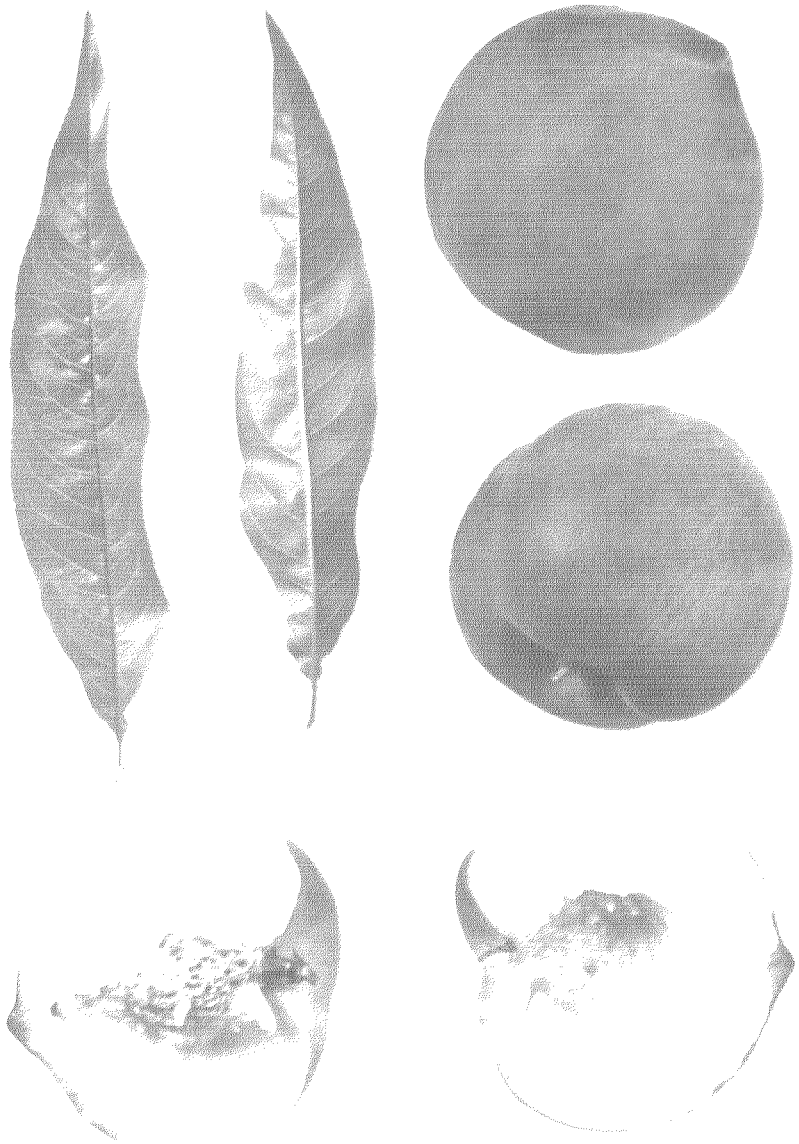
Inventor.
H. C. Swim
By: Robert Cobb
Attorney.

Patented Apr. 20, 1954

Plant Pat. 1,268

UNITED STATES PATENT OFFICE 1,268

PEACH TREE

Herbert C. Swim, Ontario, Calif., assignor to Armstrong Nurseries, Inc., Ontario, Calif., a corporation of California Application January 26, 1953, Serial No. 333,396

1 Claim. (Cl. 47—62)

The present invention relates to a new and distinct variety of peach tree which was originated by me by crossing an unnamed and unpatented peach seedling with the variety known as the "Robin Peach" (Plant Patent No. 529), the former being the seed parent and the latter being the pollen parent.

The aforementioned breeding has produced an improved variety of peach tree of the white-fleshed, semi-freestone type which is particularly characterized as to novelty by its unique combination of a short winter-chilling requirement, a short maturation period, and a very early ripening date. These qualities make the new variety especially suited to planting in Southern California and similar areas where it has the ability to produce a crop of fruit each year when winter temperatures are insufficient to satisfy the chilling requirements of standard varieties of otherwise similar type. My new variety has a chilling requirement similar to that of the "Babcock Peach" (unpatented), but it differs from the latter variety by having a much shorter maturation period and by its habit of ripening at a much earlier date.

In comparison with the seed parent, the fruit of my new variety is white-fleshed and semi-freestone, whereas that of its seed parent is yellow-fleshed and freestone; my new variety ripens from 7 to 8 weeks earlier than the fruit of the seed parent, the former ripening from about the middle of May to late May at Ontario, California, whereas the parent variety ripens from about the middle of July to late July in the same location; and the fruit of the new variety is somewhat smaller in size than that of its seed parent.

My new variety differs from its pollen parent "Robin Peach" by usually ripening about 2 weeks earlier than the fruit of this parent, and sometimes even more early; the blooms of my new variety are non-showy, whereas those of this parent are showy in type; the color of the blooms of my new variety is deep pink, while the color of the blooms of this parent is light pink; the flavor of the fruit of the new variety is typified by a substantial balance of acid and sugar, whereas the flavor of the fruit of this parent is sub-acid and predominantly sweet; and the fruit of the new variety has more contrast in skin color by reason of its being blotched and mottled, whereas the skin color of the fruit of this parent is typically a more uniform pattern of overlay.

Asexual reproduction of my new variety by budding at Ontario, California, shows that the foregoing characteristics and distinctions come true to form and are established and transmitted through succeeding propagations.

The accompanying drawing shows typical specimens of the fruit and foliage of my new variety, with both the upper side and the lower side of the foliage being illustrated, and the fruit being shown in elevation, and also in section both with and without the stone or pit.

The following is a detailed description of my new variety, based upon observations of specimens grown at Ontario, California, with color terminology in accordance with Robert F. Wilson's Horticultural Colour Chart (hereinafter designated as "Wilson"), and Ridgway's Color Standards and Nomenclature (hereinafter designated as "Ridgway"), except where general color terms of ordinary dictionary significance are obvious:

*Dates of first and last picking.*—Vary somewhat from year-to-year because of varying winter chilling in Southern California, but usually begin picking about May 12 to June 1, and ending about May 28 to June 10, depending on the season.

Tree: Large to medium size; vigorous; upright; dense; vase-formed; very productive; regular bearer.

Trunk: Medium caliper in relation to length; smooth to medium surface roughness.

Branches: Medium caliper; smooth to medium roughness; dull.

*Color.*—Near Army Brown, Plate XL (Ridgway), shaded with near Mouse Gray, Plate LI (Ridgway).

*Lenticels.*—Numerous to medium in number; medium size.

Leaves: Length 4½ inches to 5½ inches; width 1¼ inches to 1½ inches; large; acuminate to lanceolate; medium thickness; relatively smooth; wavy type (as defined in article by Meader and Blake entitled "Progress Report on Identification of Peach Varieties by Leaf Characteristics," appearing in American Society for Horticultural Science Proceedings for 1939, volume 37, pages 203 to 207).

*Color.*—Upper surface—between Deep Dull Yellow-Green (1), Plate XXXII (Ridgway) and Dark Dull Yellow-Green, Plate XXXII (Ridgway). Lower surface—near chromium Green, Plate XXXII (Ridgway).

*Margin.*—Glandular; finely serrate.

*Petiole.*—Medium length; medium caliper.

*Glands.*—Usually 2, but sometimes 3; opposite; medium to small size; globose; position usually found on margin of leaf near attachment of leaf blade to petiole. Color—near Calliste Green, Plate VI (Ridgway).

*Stipules.*—Medium length; narrow; early deciduous.

Flower-buds: Medium to small size; conic-pointed; medium length; pubescent, with bud scales having yellowish pubescence and free portion of calyx having grayish pubescence on outside surface.

Flowers: Dates first and full bloom—first bloom about February 24 to March 14; full bloom about March 16 to March 24; medium early as compared with other varieties; medium to small size; non-showy in type. Color of newly opened flower—between Neyron Rose, Plate 623/1, page 76 (Wilson) and Phlox Pink, Plate 625/1, page 77 (Wilson).

Fruit: Maturity when described—eating ripe. Date—June 2.

*Size.*—Usually uniform; medium to small. Axial diameter—1⅞ inches to 2⅜ inches. Transverse diameter in suture plane—1⅞ inches to 2¼ inches. Diameter at right angles to suture plane—2 inches to 2¼ inches.

*Form.*—Uniform; symmetrical; globose.

*Suture.*—Usually an inconspicuous shallow line extending from base to apex, but discontinuous at apex; has slight depression beyond pistil point.

*Ventral surface.*—Rounded; slightly lipped on right or left sides; lips sometimes slightly unequal, but often quite inconspicuous.

*Stem cavity.*—Rounded to slightly elongated in suture plane, with suture showing on one side; depth $\frac{3}{16}$ inch; breadth ½ inch.

*Base.*—Rounded.

*Apex.*—Short; rounded. Pistil point—short; apical.

*Stem.*—Length ¼ inch; medium caliper. Adherence to stone—medium.

*Skin.*—Medium to thin; medium texture; more or less free. Tendency to crack—none observed. Color—basic color near Buttercup Yellow, Plate 5/3, page 5 (Wilson), overlaid with between Delft Rose, Plate 020/1, page 108 (Wilson) and Delft Rose, Plate 020/2, page 108 (Wilson); heavily streaked with between Currant Red, Plate 821/1, page 167 (Wilson) and Cardinal Red, Plate 822/1, page 168 (Wilson). Down—moderate; short; rolls up when rubbed.

*Flesh.*—Color—between White and Amber Yellow, Plate 505/3, page 132 (Wilson), with flecks and stripes or blotches of near Geranium Lake, Plate 20/1, page 20 (Wilson); surface of pit cavity between White and Amber Yellow, Plate 505/3, page 132 (Wilson). Amygdalin—scant. Juice—abundant; rich. Texture—medium firmness; fine; melting. Fibers—medium size; tender. Ripens—usually even. Flavor—acid to sub-acid; a good blend of sugar and acid. Aroma—not pronounced. Eating quality—good.

Stone: Semi-free; adheres to flesh somewhat over entire surface when firm, but usually along only both dorsal and ventral edges when fully ripe; fibers long to medium; free usually on sides when fully ripe; fibers in depressions of pit.

*Size.*—Medium to small; length 1¼ inches to 1⅜ inches; breadth ¾ inch to ⅞ inch.

*Thickness.*—⅝ inch to ⅞ inch.

*Form.*—Ovoid; cuneate toward apex; base straight; hilum oval; apex acute.

*Sides.*—Slightly unequal; curved on right and left sides; surface irregularly furrowed toward apex; ridged toward apex; pitted from base to above center.

*Ridges.*—Usually rounded toward apex.

*Pits.*—Elongated.

*Ventral edge.*—Thick, with wing throughout.

*Dorsal edge.*—Medium, with shallow, narrow groove to above center and with interrupted ridges on either side.

*Color of stone.*—Between Cream Buff, Plate XXX (Ridgway) and Colonial Buff, Plate XXX (Ridgway).

*Tendency to split.*—Very slight.

Use: Market; local; dessert.

Keeping quality: Medium.

Resistance to:

*Insects.*—Medium resistance to thrips, as determined by comparison with other varieties grown under comparable cultural conditions at Ontario, California.

*Diseases.*—No disease susceptibility observed at Ontario, California.

Shipping quality: Medium.

I claim:

A new and distinct variety of peach tree of the white-fleshed, semi-freestone fruit type, substantially as herein shown and described, characterized particularly as to novelty by its short winter-chilling requirement, by its short maturation period, and by its very early ripening date.

No references cited.